US010725281B2

(12) United States Patent
Thursby et al.

(10) Patent No.: US 10,725,281 B2
(45) Date of Patent: Jul. 28, 2020

(54) OPTICAL CAP FOR A WELLBORE INSPECTION ASSEMBLY

(71) Applicant: E.V. OFFSHORE LIMITED, Norwich, Norfolk (GB)

(72) Inventors: Jonathan Thursby, Norwich (GB); Shaun Peck, Norwich (GB)

(73) Assignee: E.V. OFFSHORE LIMITED, Norwich (GB)

( * ) Notice: Subject to any disclaimer, the term of this patent is extended or adjusted under 35 U.S.C. 154(b) by 57 days.

(21) Appl. No.: 16/072,703

(22) PCT Filed: Jan. 19, 2017

(86) PCT No.: PCT/GB2017/050136
§ 371 (c)(1),
(2) Date: Jul. 25, 2018

(87) PCT Pub. No.: WO2017/129950
PCT Pub. Date: Aug. 3, 2017

(65) Prior Publication Data
US 2019/0079279 A1    Mar. 14, 2019

(30) Foreign Application Priority Data
Jan. 26, 2016 (GB) ................... 1601452.4

(51) Int. Cl.
*H04N 7/18*         (2006.01)
*G02B 23/24*        (2006.01)
(Continued)

(52) U.S. Cl.
CPC ........ *G02B 23/2423* (2013.01); *A61B 1/0008* (2013.01); *A61B 1/0011* (2013.01);
(Continued)

(58) Field of Classification Search
CPC ............ G02B 23/2423; G02B 23/2476; G02B 23/24; G02B 23/2461; G02B 23/2492;
(Continued)

(56) References Cited

U.S. PATENT DOCUMENTS 4,793,864 A * 12/1988 Neumiller ............... C07C 49/83
                                                        134/1
2005/0239227 A1* 10/2005 Aanegola ................ H01L 33/52
                                                        438/26
(Continued)

FOREIGN PATENT DOCUMENTS

CN     203331037 U    12/2013
DE     102012103960 A1   11/2013
(Continued)

OTHER PUBLICATIONS

Shukla et al, A review of robotics in onshore oil-gas industry (Year: 2013).*
(Continued)

*Primary Examiner* — Shan E Elahi
(74) *Attorney, Agent, or Firm* — Hayes Soloway PC

(57) ABSTRACT

An optical cap that protects a camera lens of the inspection assembly is disclosed herein. The disclosed optical cap for an inspection assembly may include an optically clear dome-shaped window element and a metal collar attached to the window element, the collar including means for securing the optical cap to said inspection assembly, wherein the collar is bonded to the window element by means of brazing or welding.

22 Claims, 4 Drawing Sheets

(51) Int. Cl.
*E21B 47/00* (2012.01)
*A61B 1/00* (2006.01)
*G01N 21/954* (2006.01)

(52) U.S. Cl.
CPC ...... *A61B 1/00089* (2013.01); *A61B 1/00096* (2013.01); *A61B 1/00101* (2013.01); *A61B 1/00174* (2013.01); *E21B 47/0002* (2013.01); *G01N 21/954* (2013.01); *G02B 23/24* (2013.01); *G02B 23/2461* (2013.01); *G02B 23/2492* (2013.01)

(58) Field of Classification Search
CPC .............. G01N 21/954; A61B 1/00101; A61B 1/00089; A61B 1/0008; A61B 1/00174; A61B 1/0011; A61B 1/00096; E21B 47/0002
USPC .......................................................... 348/65
See application file for complete search history.

(56) References Cited

U.S. PATENT DOCUMENTS

| | | | |
|---|---|---|---|
| 2006/0268549 A1* | 11/2006 | Oehlke | F21S 10/06 362/276 |
| 2007/0018175 A1* | 1/2007 | Mazzochette | H01L 33/60 257/81 |
| 2008/0143822 A1 | 6/2008 | Wang et al. | |
| 2008/0177646 A1* | 7/2008 | Frink | G06Q 10/1091 705/32 |
| 2008/0262309 A1 | 10/2008 | Miyoshi et al. | |
| 2009/0262517 A1* | 10/2009 | Suehiro | G02B 6/0023 362/84 |
| 2010/0033986 A1 | 2/2010 | Schober et al. | |
| 2011/0180197 A1 | 7/2011 | Akagi et al. | |
| 2011/0281122 A1* | 11/2011 | Bayya | C03C 3/253 428/432 |
| 2013/0043168 A1* | 2/2013 | Dufilho | B01D 33/0315 209/365.1 |
| 2013/0155214 A1* | 6/2013 | Yamane | A61B 1/00172 348/65 |
| 2013/0287380 A1 | 10/2013 | Thursby et al. | |
| 2014/0158199 A1* | 6/2014 | Vasylyev | G02B 19/0004 136/259 |
| 2015/0281526 A1* | 10/2015 | Hovland | E21B 47/0002 348/92 |
| 2017/0051884 A1* | 2/2017 | Raring | H01S 5/02236 |

FOREIGN PATENT DOCUMENTS

| | | | | |
|---|---|---|---|---|
| EP | 1972256 A1 | 9/2008 | | |
| GB | 2485767 A | 5/2012 | | |
| JP | 2007222642 A | 9/2007 | | |
| JP | 2010055023 A | * | 3/2010 | ............... A61B 1/00 |
| KR | 20130005631 A | 1/2013 | | |
| WO | 2014068042 A1 | 5/2014 | | |

OTHER PUBLICATIONS

Fotronic Corporation; "Wohler VIS 340 Visual Inspection System with mini USB port & built-in recorder"; Test Equipment Depot; Jul. 22, 2012; p. 1-3.

Advanced Inspection Technologies Inc.; "Glass Dome for Pan & Tilt Camera Head"; Advanced Inspection Technologies; Dec. 17, 2015; p. 1-2.

\* cited by examiner

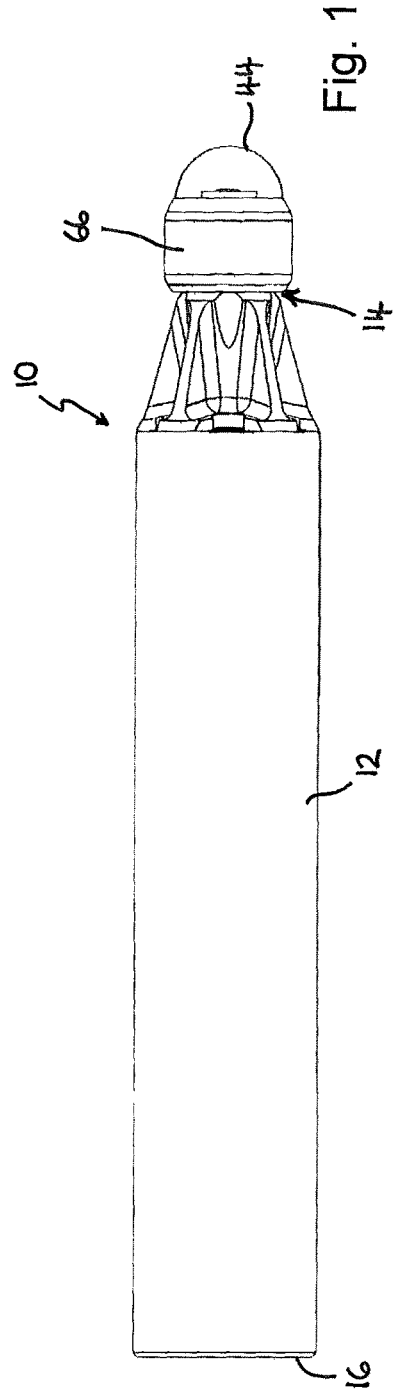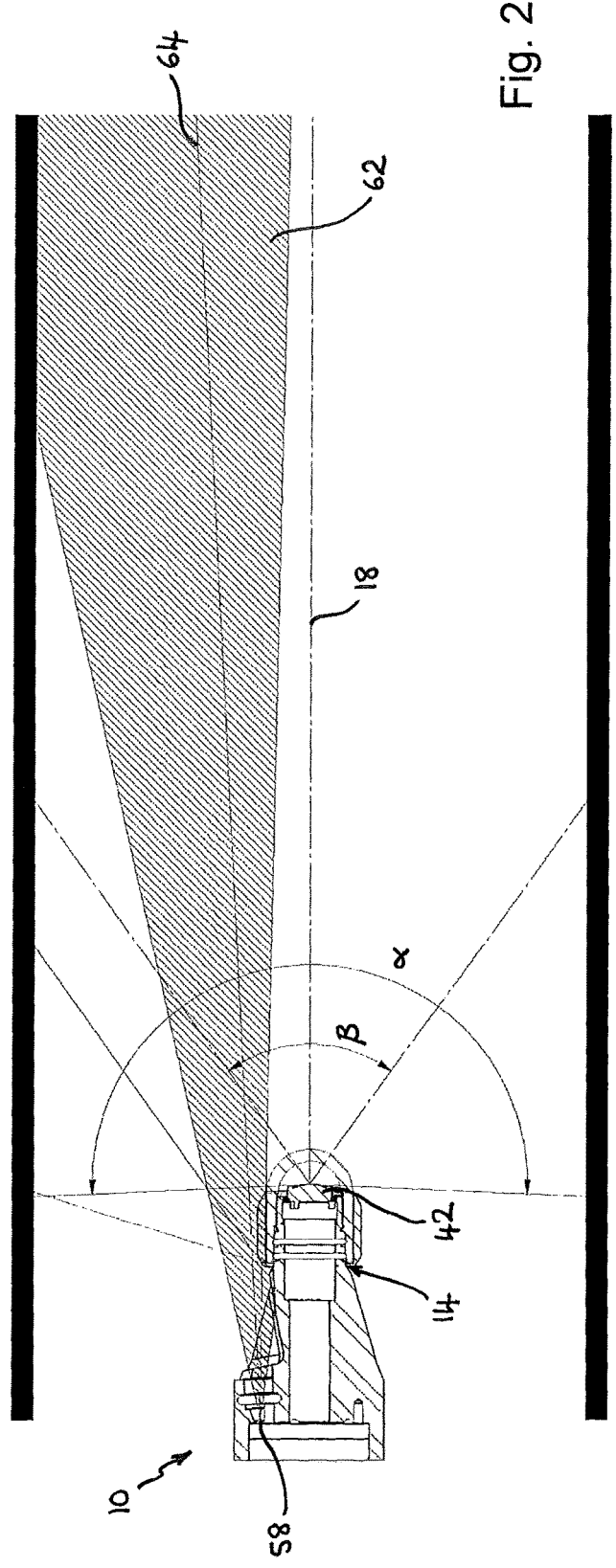

OPTICAL CAP FOR A WELLBORE INSPECTION ASSEMBLY

CROSS REFERENCE TO RELATED APPLICATIONS

This application is a U.S. National phase entry under 35 U.S.C. § 371 of International Application No. PCT/GB2017/050136, filed on Jan. 19, 2017, which claims priority to Great Britain Patent Application 1601452.4, filed on Jan. 26, 2016. Each of these patent applications is incorporated by reference herein in its entirety.

BACKGROUND a. Field of the Invention

This invention relates to an optical cap for an inspection assembly. In particular this invention relates to the provision of an optical cap that protects a camera lens of the inspection assembly. This invention further relates to a method of manufacturing an optical cap and to an inspection assembly including an optical cap. The invention is particularly suited to inspection assemblies and camera systems that operate in high temperature and high pressure environments, such as those that operate downhole.

b. Related Art

Systems and assemblies for inspecting internal spaces such as interior walls of pipelines or similar are known. When these systems are used downhole, for example in offshore environments, an inspection assembly comprising a source of illumination and a camera are lowered through the pipeline or conduit and the camera is configured to capture images of the internal surfaces of the pipeline. In this way the inspection system may be used to visualise the condition of the pipeline to determine if remedial action is required.

Pipelines or wellbores can reach depths of hundreds or thousands of metres and inspection assemblies may be required to withstand significant temperatures and pressures. Pressures at depth in a wellbore can reach around 150 MPa and temperatures may exceed 100° C.

In some inspection systems the camera and in particular the camera lens is located in a nose region of the assembly and is forward facing. In this way, the camera is able to capture images of the interior of the pipeline ahead of the inspection assembly as it is lowered or moved through the pipeline. In these systems it is necessary to provide a suitable cover and/or sealing arrangement to protect the inspection system from the environment of the pipeline and, in particular, to protect the vulnerable camera lens.

In order to provide even illumination of the field of view of the camera, the light sources are often located behind the camera lens and are angled in a direction towards the internal wall of the pipeline ahead of the inspection assembly. In this way the walls of the pipeline are illuminated at a distance from the front of the inspection assembly.

In some systems it is desirable to use a wide angle lens, such as a fish-eye lens. When existing systems are retrofitted with such a wide angle lens, however, the configuration of the light sources may be such that there is inadequate illumination of the entire field of view. In particular the periphery of the image may be under exposed and the central portion of the image may be over exposed.

It is, therefore, an object of the present invention to provide an assembly that overcomes at least some of the disadvantages of prior art assemblies, whether referred to herein or otherwise.

SUMMARY OF THE INVENTION

According to a first aspect of the present invention there is provided an optical cap for a wellbore inspection assembly comprising a main body having a longitudinal axis and a forward end, a lens located at the forward end, and a light source disposed rearward of the lens and positioned to illuminate an area forward of the lens, the optical cap comprising:

an optically clear window element comprising a domed portion and an attachment portion including an end face; and a metal collar including means for securing the optical cap to said inspection assembly such that, in use, light entering the lens passes through the window element of the optical cap, the collar being bonded to the window element by means of brazing, welding or fusing and at least a part of the collar surrounding the attachment portion of the window element such that, in use, a part of the collar blocks light that is emitted by the light source and that would otherwise be incident on the end face of the window element from entering the window element.

Preferably the material from which the window element is made has substantially the same coefficient of thermal expansion as the metal from which the collar is made.

The collar may be bonded to the window element by means of energy beam welding, solid state welding and/or brazing.

The window element is preferably made of sapphire, quartz or diamond. The collar is preferably made of titanium.

The collar may be bonded to a base edge of the window element. Alternatively or additionally the collar may be bonded to an external surface of the window element.

Typically the collar is substantially tubular and an external diameter of the collar is preferably between 25 mm and 35 mm.

In preferred embodiments the collar comprises a ring element and a sleeve element. The sleeve element preferably includes the means for securing the optical cap to the inspection assembly. The ring element is preferably bonded to the window element and the sleeve element is preferably bonded to the ring element. Advantageously an outer surface of the ring element is continuous with an outer surface of the sleeve element.

The ring element may include a radially inwardly extending rib. In these embodiments the window element is preferably in contact with a first side of the rib and the sleeve element is preferably in contact with an opposite second side of the rib. Alternatively or additionally, an internal surface of a first portion of the ring element may be in contact with an external surface of the window element and an internal surface of a second portion of the ring element may be in contact with an external surface of the sleeve element.

Preferably a first end of the ring element extends beyond a first end of the sleeve element, and the window element extends beyond the first end of the ring element.

The means for securing the optical cap to said inspection assembly preferably comprises a screw thread. The screw thread is preferably provided on an internal surface of the sleeve element in embodiments in which this is provided.

In particularly preferred embodiment the collar comprises a sleeve element having first and second ends defining an axis of the collar, the window element being located proximate the first end, and a reflection surface at the second end of the sleeve element, an angle between the reflection surface and the axis of the collar being between 10° and 70°. The reflection surface may be an unpolished surface of the collar.

According to a second aspect of the present invention there is provided a wellbore inspection assembly comprising:

a main body having a longitudinal axis and a forward end;
a lens located at the forward end of the main body;
a light source disposed rearward of the lens and arranged to illuminate an area forward of the lens; and
an optical cap comprising an optically clear window element and a metal collar, the window element comprising a domed portion and an attachment portion including an end face, and the collar being bonded to the window element by brazing, welding or fusing,
the optical cap being secured to the main body such that the window element extends over the lens and light entering the lens passes through the window element of the optical cap,
and wherein a part of the collar blocks light that is emitted by the light source and that would otherwise be incident on the end face of the window element from entering the window element.

Preferably the lens is a wide angle lens or a fish-eye lens.

The inspection assembly preferably comprises a plurality of light sources arranged around the main body and radially outward of the lens. In these embodiments the optical cap preferably comprises a sleeve element having first and second ends, the window element being located proximate the first end and a reflection surface being provided at the second end. The reflection surface is, therefore, located between the light sources and the lens.

The location of the reflection surface causes a part of a light beam emitted from a light source to be deflected such that an angle between the direction of travel of the deflected light beam and the longitudinal axis of the assembly is greater than the angle between a direction of travel of a non-deflected light beam and the longitudinal axis.

When the inspection assembly is located in a pipeline or conduit, the fraction of the emitted light that is deflected or reflected, therefore, illuminates a region of the interior walls of the pipeline closer to the inspection assembly. This creates a more even illumination of the field of view if a wide angle lens is used in the inspection assembly. In order to still provide adequate illumination of the central region of the field of view, however, it is preferable if the fraction of the emitted light that is deflected or reflected is less than 50% of the total emitted light.

Furthermore, when present, the reflection surface is located such that the emitted light that is incident on the reflection surface is reflected in a direction substantially away from the window element. As such, the likelihood of light directly entering the window element and being internally reflected or refracted is significantly reduced.

The inspection assembly preferably further comprises an image sensor arranged to capture an image of a field of view through the lens. The inspection assembly may additionally include a memory for storing the captured image data or a transmitter for transmitting the image data to a remote receiver in real time.

BRIEF DESCRIPTION OF THE DRAWINGS

The invention will now be further described by way of example only and with reference to the accompanying drawings, in which:

FIG. 1 is a side view of an inspection assembly including an illumination collar;

FIG. 2 shows the inspection assembly of FIG. 1 in a passageway and illustrates a field of view of a camera and a region of illumination of a light source of the inspection assembly;

DETAILED DESCRIPTION

Figure 3:
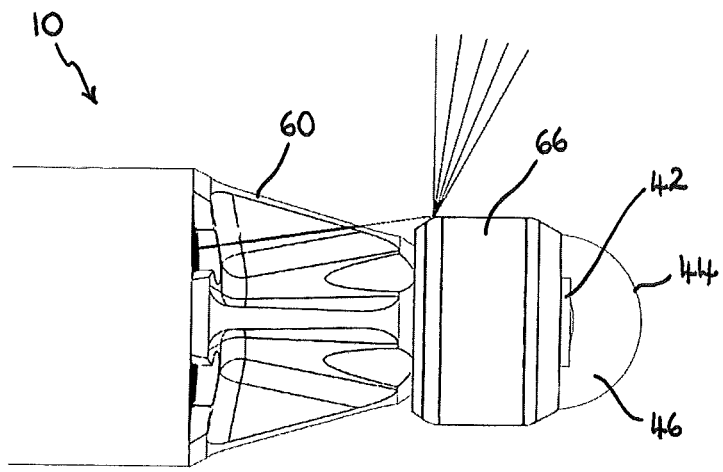
FIG. 3 is a side view of a distal end region of the inspection assembly of FIG. 1 showing reflection and diffusion of a light beam striking the illumination collar.

Inspection assemblies or camera systems used to inspect passageways such as pipelines and wellbores typically include a camera and one or more light sources arranged to light the field of view of the camera. Often these are housed in a first, distal end region of an elongate cylindrical housing which is lowered down the wellbore by cables or a shaft attached at a second end. In most cases, the camera systems will also include a viewport or window at or near the distal end of the camera housing that serves to protect the camera.

In use, when an inspection assembly is deployed along a passageway, the distal end of the assembly will be a front end with respect to a direction of travel of the assembly. Accordingly, in the following description the terms front end, forward facing or similar will be used to describe or refer to elements that are located at or near the first, distal end of the assembly or that face in a direction towards the distal end. Similarly, the terms rear end, rearward facing or similar denote elements that are located at or near the second, proximal end of the assembly or that face in a direction towards the second end.

A preferred embodiment of an inspection assembly 10 according to the present invention is illustrated in FIGS. 1 to 4. The inspection assembly 10 includes an elongate main body 12 having a first, distal end 14 and a second, proximal end 16. The first and second ends 14, 16 define a longitudinal axis 18 of the inspection assembly 10.

An end region 20 of the main body 12 at the distal end 14 comprises a light emitting portion 22, a light guide portion 24 and a nose portion 26. The nose portion 26 includes a distal end face 28 of the main body 12. The end region 20 is generally tapered such that an external diameter of the main body 12 at the light emitting portion 22 is greater than the external diameter of the nose portion 26.

A decrease in diameter of the light emitting portion 22 creates a shoulder 30 having a generally forward facing surface 32. A plurality of apertures 34 are formed in the shoulder 30. The apertures 34 are sealed by transparent windows or viewports 36. The apertures 34 are preferably in a substantially circular or annular arrangement around the shoulder 30.

A bore 38 extends longitudinally through the end region 20 and terminates at an aperture 40 in the distal end face 28. A lens 42 is mounted in the aperture 40. The lens 42 is preferably an ultra wide angle lens such as a fish-eye lens. The fish-eye lens will typically have an angle of view (α) of about 185°, compared to a standard lens having an angle of view (β) of about 74°, as illustrated in FIG. 2. In this embodiment, including a fish-eye lens 42, a part of the lens 42 projects forward of the distal end face 28 so that the angle of view or field of view is not obstructed by the end face 28 of the main body 12.

The inspection assembly 10 further comprises a camera including an image sensor arranged to capture an image of the field of view through the lens 42. Accordingly, the camera captures an image of a region substantially ahead or in front of the distal end 14 of the inspection assembly 10. It will be appreciated that if an ultra wide angle lens 42 is used, having an angle of view of greater than 180°, the periphery of the image may include a region located substantially parallel with or a small distance behind the distal end face 28 of the inspection assembly 10.

Figure 4:
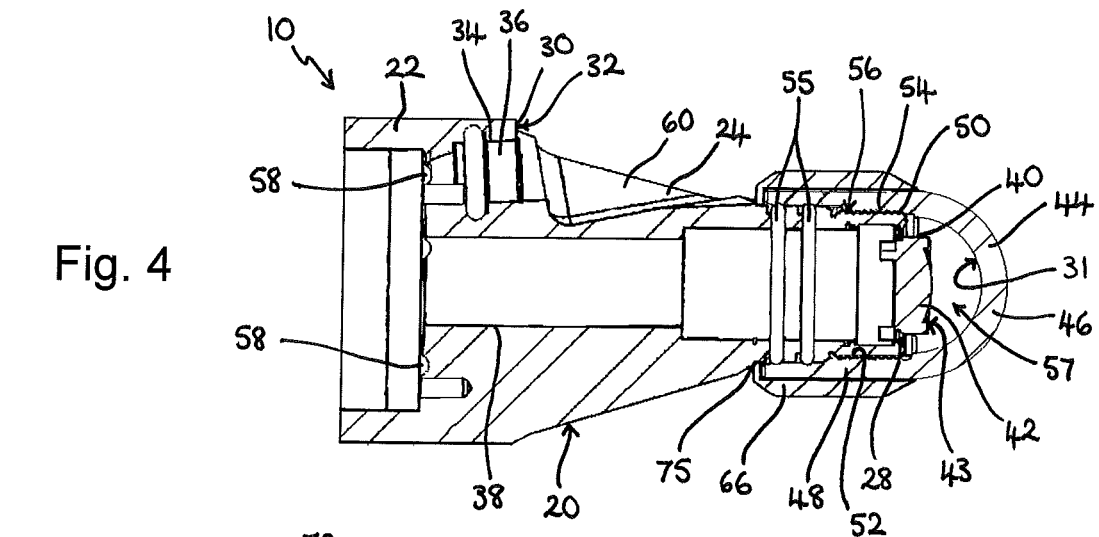
FIG. 4 is a cross sectional view of an end of the inspection assembly of FIG. 1 showing the position of the illumination collar with respect to the light source and camera lens of the inspection assembly.

To protect the lens 42, the inspection assembly 10 includes an optical cap 44, shown most clearly in FIG. 4. The cap 44 comprises a hemi-spherical or dome-shaped window portion 46 and a tubular attachment portion 48. At least the window portion 46 is optically transparent. Typically the cap 44 will be a unitary piece such that both the window portion and the attachment portion are made of the same transparent material. In this embodiment the cap 44 is made of a suitable acrylic material.

The attachment portion 48 includes a female securing feature in the form of a screw thread 50 on an internal surface 52 of the attachment portion 48. A corresponding male securing feature in the form of a screw thread 54 is provided on an external surface 56 of the nose portion 26 of the main body 12. The cap 44 is, therefore, secured to the main body 12 by engaging the complementary screw threads 50, 54. Once engaged, the attachment portion 48 of the cap 44 extends around the nose portion 26 of the main body 12. Sealing elements such as o-rings 55 may be provided to form a seal between the external surface 56 of the nose portion 26 and the internal surface 52 of the cap 44.

With the cap 44 secured to the main body 12 the window portion 46 extends beyond the distal end face 28 of the nose portion 26. In particular the domed window portion 46 extends over the lens 42 such that there is a gap 57 between a front face 43 of the lens 42 and an internal surface 31 of the window portion 46 of the cap 44.

The inspection assembly 10 further comprises a plurality of light sources 58 mounted in the light emitting portion 22 of the main body 12. The light sources 58 are preferably light emitting diodes (LEDs). Each of the light sources 58 is arranged to emit a beam of light through a corresponding one of the apertures 34. As such, the light sources 58 are substantially forward facing and the light emitted by the light sources 58 travels in a direction that illuminates an area ahead of or in front of the distal end 14 of the inspection assembly 10.

The light guide portion 24 of the end region 20 comprises a plurality of radially extending webs or ribs 60. Light guide channels are defined between neighbouring ribs 60. Each channel is aligned with one of the apertures 34.

As shown in FIG. 2, each light source 58 emits a diverging beam of light 62. A direction of the emitted light is defined by a centre line 64 of the light beam 62. The beam divergence angle is preferably between 10° and 30°, and most preferably about 20°.

Figure 5:
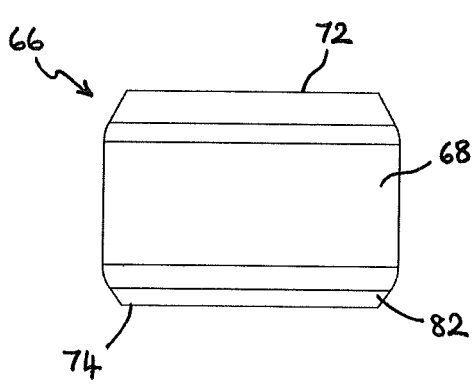
FIG. 5 is a side view of the illumination collar of FIG. 1.
Figure 6:
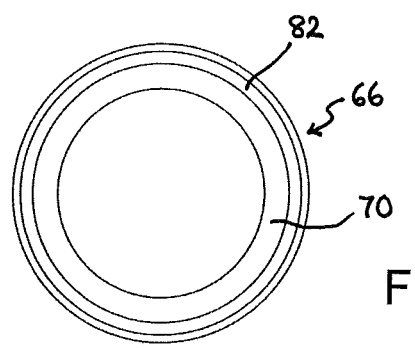
FIG. 6 is an end view from a second end of the illumination collar of FIG. 5.
Figure 7:
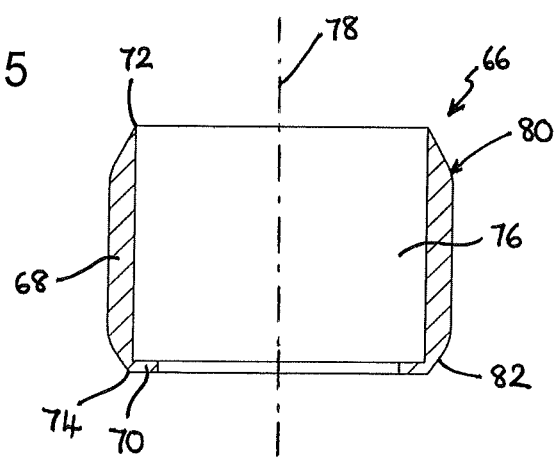
FIG. 7 is a longitudinal sectional view of the illumination collar of FIG. 5.

A reflection collar 66 is located over and around the attachment portion 48 of the cap 44. As shown in FIGS. 5 to 7, the collar 66 comprises a sleeve portion 68 and retaining means in the form of a retaining flange 70. The sleeve portion 68 is substantially tubular and extends between first and second ends 72, 74. A bore 76 of the sleeve portion 68 extends along an axis 78 of the collar 66. The retaining flange 70 projects radially inwardly from the second end 74 of the sleeve portion 68.

In a preferred embodiment the collar 66 has a circular cross-sectional shape. An internal diameter of the sleeve portion 68 is constant along the length of the sleeve portion 68 and is sized to receive the attachment portion 48 of the cap 44. An external surface 80 of the collar 66 at the first end 72 is tapered.

The external surface 80 of the collar 66 is also tapered at the second end 74. This tapered portion of the surface 80 provides a reflection surface 82. An angle between the reflection surface 82 and the axis 78 of the collar 66 is preferably greater than 10° and less than 70°. The angle between the reflection surface 82 and the axis 78 may be more than 20° or more than 30°. The angle between the reflection surface 82 and the axis 78 may be less than 60°, less than 50° or less than 40°. Most preferably the angle is between 30° and 40° and will typically be about 36°.

The collar 66 is preferably made from a metallic material, and will typically be made from a suitable grade of stainless steel. The reflection surface 82 is preferably unpolished. This causes the light that is reflected from the surface 82 to be diffused, as illustrated in FIG. 3.

To attach the reflection collar 66 to the main body 12 of the inspection assembly 10, the collar 66 is fitted over the nose portion 26 of the main body 12 with the second end 74 of the collar 66 nearest the light sources 44. The collar 66 is prevented from moving further along the end region 20 of the main body 12 by an abutment surface 75 of the main body 12.

The reflection surface 82 of the collar 66 is, therefore, located between the light sources 58 and the lens 42 in a longitudinal direction. The reflection surface 82 is substantially rear facing so that a fraction of the light that is emitted by the light sources 58 is incident on the reflection surface 82.

The cap 44 is screwed onto the nose portion 26 of the main body 12 such that the attachment portion 48 is located between the sleeve portion 68 of the collar 66 and the nose portion 26. The cap 44 is screwed onto the nose portion 26 until an end 49 of the attachment portion 48 contacts the flange 70 of the collar 66 and the flange 70 of the collar 66 is in contact with the abutment surface 75. In this way, with the collar 66 and cap 44 fully attached to the main body 12, the flange 70 is clamped between the abutment surface 75 of the main body 12 and the end 49 of the cap 44, thereby retaining the collar 66 on the main body 12. Furthermore, in this position the flange 70 extends over and covers the end 49 of the cap 44. In this way, the flange 70 blocks light emitted by the light sources 58 that would otherwise be incident on the end 49 of the cap 44.

The length of the collar 66, between the first and second ends 72, 74, is such that the first end 72 of the collar 66 does not extend beyond the front face 43 of the lens 42. In this way the collar 66 does not block the field of view of the lens 42. The collar 66 does, however, fully surround at least a part of the attachment portion 48 of the cap 44 thereby protecting this part of the cap 44 from damage.

The light sources 58 are arranged such that the centre lines 64 of the light beams 62 fall on a circle having a diameter greater than the external diameter of the collar 66. In this way, at least 50% of the light emitted by the light sources 58 passes around the collar 66 without being reflected or deflected by the reflection surface 82.

A fraction of the light emitted by each of the light sources 58 is incident on the reflection surface 82. The angle of the reflection surface 82 causes the light to be reflected in a direction away from the axis 18 of the inspection assembly 10. In particular, a fraction of the light beam 62 located between the main body 12 of the inspection assembly 10 and the centre line 64 of the light beam 62 is reflected by the reflection surface 82.

Figure 8:
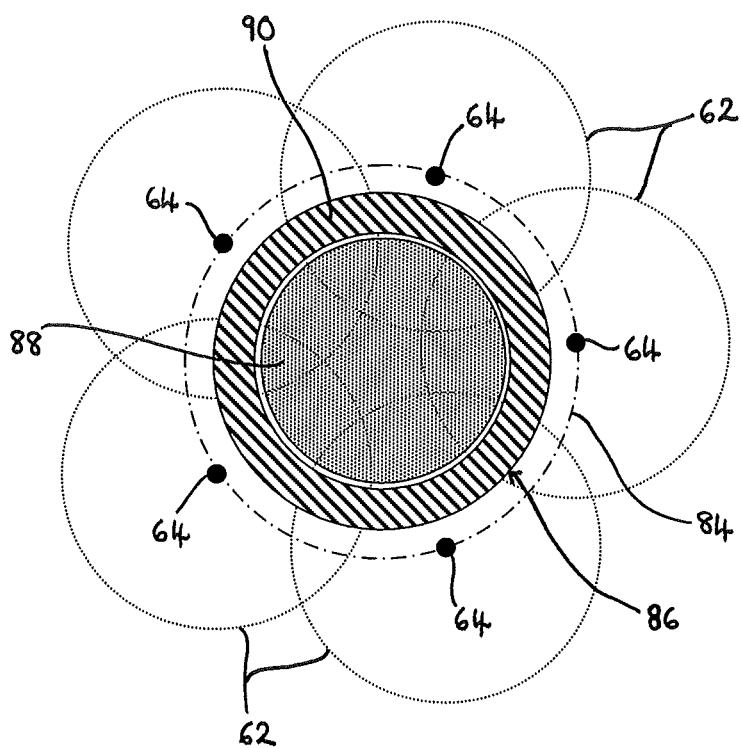
FIG. 8 illustrates an illumination pattern resulting from an annular arrangement of five light sources of the inspection assembly of FIG. 1.

This is illustrated in FIG. 8 which shows the illumination pattern resulting from an annular arrangement of five light sources emitting divergent beams of light 62.

The centre line 64 of each of the beams of light 62 lies on a circle 84 having a diameter greater than the external diameter 86 of the collar. The central shaded region 88 in FIG. 8 denotes the part of each of the light beams 62 that is incident on a part of the inspection assembly 10 and does not reach the field of view of the lens 42. The hatched region 90 denotes the fraction of each of the light beams 62 that strikes the reflection surface 82 and is reflected outwardly to a peripheral region of the field of view.

It can be seen that the result of reflecting a radially inner portion 90 of each of the light beams 62 is that the overall intensity of the light in a central region of the field of view is decreased while the overall intensity of the light in a peripheral region of the field of view is increased. In this way the field of view is more evenly illuminated decreasing the likelihood that regions of an image captured by the camera will be underexposed or overexposed.

Figure 9:
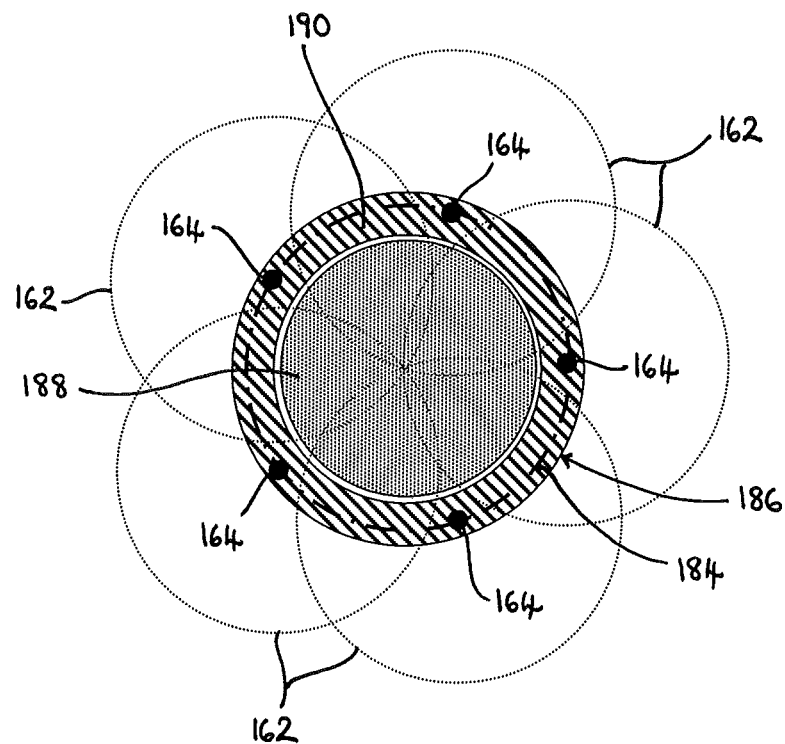
FIG. 9 illustrates an alternative illumination pattern resulting from an annular arrangement of five light sources.

In other embodiments the light sources may be arranged such that centre lines 164 of light beams 162 emitted by the light sources fall on a circle having a diameter smaller than the external diameter of the collar. This is illustrated in FIG. 9 which shows the illumination pattern resulting from an annular arrangement of five light sources emitting divergent beams of light 162. The centre line 164 of each of the beams of light 162 lies on a circle 184 having a diameter smaller than the external diameter 186 of the collar. The central shaded region 188 in FIG. 9 denotes the part of each of the light beams 162 that is incident on a part of the inspection assembly 10 and does not reach the field of view of the lens 42. The hatched region 190 denotes the fraction of each of the light beams 162 that strikes the reflection surface 82 and is reflected outwardly to a peripheral region of the field of view. In some of these embodiments at least 50% of the light emitted by the light sources 58 passes around the collar 66 without being reflected or deflected by the reflection surface 82. In one particular embodiment the diameter of the circle 184 on which the centre line 164 of each of the beams of light 162 lies is approximately 28 mm and the external diameter 186 of the collar is approximately 30 mm.

It will be appreciated that although the reflection surface 82 has been described as being part of an illumination collar 66 that is separate from the main body 12 of the inspection assembly 10, in other embodiments the reflection surface 82 may be provided on the main body 12 or may be provided by another component of the inspection assembly 10. The reflection surface may be provided on the optical cap. Furthermore, in some embodiments, the collar 66 may be attached or secured directly to the main body 12 rather than being secured by means of the cap 44 as described above. Accordingly, in these embodiments the collar 66 may include means for securing the collar 66 to the main body 12, for example by means of screw threads.

Figure 10:
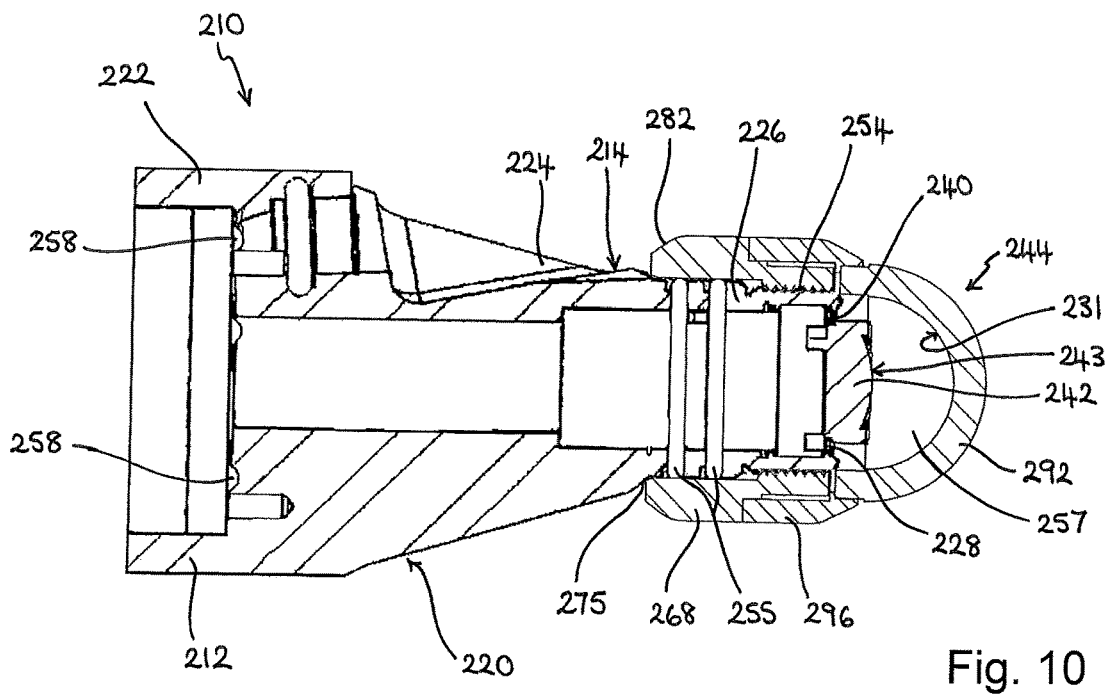
FIG. 10 is a cross sectional view of an end of an inspection assembly showing an optical cap according to a preferred embodiment of the present invention.

FIG. 10 shows another embodiment of an inspection assembly 210. Many of the features of this embodiment are the same as or similar to features of the previous embodiment and like features are indicated by reference numerals incremented by 200.

As described above, an end region 220 of a main body 212 of the inspection assembly 210 at a distal end 214 comprises a light emitting portion 222, including a plurality of light sources 258, a light guide portion 224 and a nose portion 226.

A lens 242 is mounted in an aperture 240 in a distal end face 228 of the nose portion 226. The lens 242 is preferably a wide angle lens and it is advantageous if the lens 242 projects forward of the distal end face 228 so that the angle of view of the lens 242 is not obstructed by the end face 228 of the main body 212.

To protect the lens 242, the inspection assembly 210 includes an optical cap 244 attached to the nose portion 226. Additional views of the optical cap 244 are provided in FIGS. 11 and 12.

The optical cap 244 includes an optically transparent window element 292 and a collar 266. In this embodiment the collar 266 comprises a sleeve element 268 and a ring element 296. The window element 292 is made of a suitable optically transparent material that is able to withstand the high temperatures, high pressures and other harsh environments that may be encountered in use, for example in a downhole environment. In preferred embodiments the window element 292 is made of sapphire, quartz or diamond. Both the sleeve element 268 and the ring element 296 are made of a suitable metal material. In a preferred embodiment the sleeve element 268 and the ring element 296 are made of titanium. Importantly the materials from which the window element 292 and the collar 266 (the sleeve element 268 and/or the ring element 296) are made should have substantially the same coefficient of thermal expansion. This means that the difference between the coefficient of thermal expansion of the material of the window element 292 and the coefficient of thermal expansion of the material of the collar 266 should be no more than $10 \times 10^6 (° C.)^{-1}$, preferably no more than $5 \times 10^6 (° C.)^{-1}$, and most preferably no more than $2 \times 10^6 (° C.)^{-1}$.

Figure 11:
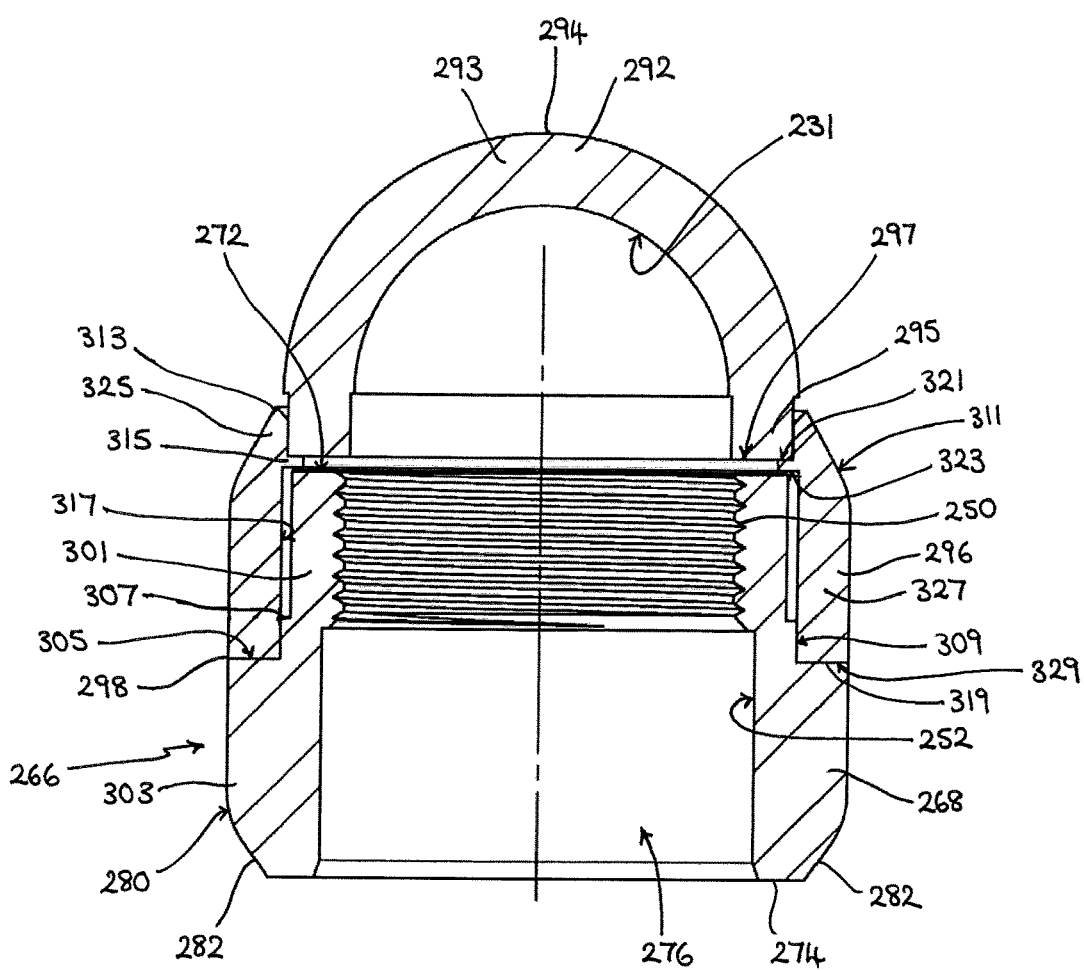
FIG. 11 is an enlarged cross-sectional view of the optical cap of FIG. 10.

The window element 292 includes a domed portion 293 and an attachment portion 295. The attachment portion 295 is integral with the domed portion 293. The attachment portion 295 is annular and extends from the domed portion 293 to provide a base end face 297 of the window element 292 furthest from the apex or crown 294 of the domed portion 293. Preferably the domed portion 293 of the window element 292 is hemispherical. In some embodiments, and as illustrated in FIG. 11, the radial thickness of the attachment portion 295 may be less than the radial thickness of the domed portion 293 such that an inner radius of the attachment portion 295 is greater than an inner radius of the domed portion 293 and an outer radius of the attachment portion 295 is smaller than an outer radius of the domed portion 293.

The sleeve element 268 is tubular, and has a circular cross-sectional shape. A central bore 276 extends through the sleeve element 268 from a first end 272 to a second end 274, thereby defining a longitudinal axis 278 of the sleeve element 268. The sleeve element 268 includes means for securing the sleeve element 268, and therefore the optical cap 244, to the main body 212 of the inspection assembly 210. In this embodiment the means comprises a screw thread 250 formed on an internal surface 252 of the sleeve element 268 proximate the first end 272 of the sleeve element 268. The screw thread 250 does not extend for the full length of the sleeve element 268 and, in this example, the diameter of the threaded region is smaller than the diameter of a non-threaded section of the bore 276 proximate the second end 274 of the sleeve element 268.

An outer surface 280 of the sleeve element 268 includes a step 298 such that an outer diameter of a first section 301 of the sleeve element 268 on a first side of the step 298 proximate the first end 272 of the sleeve element 268 is smaller than an outer diameter of a second section 303 of the sleeve element 268 on a second side of the step 298 proximate the second end 274 of the sleeve element 268.

The step 298, therefore, provides an abutment surface 305, which in this embodiment is annular and is substantially perpendicular to the axis 278 of the sleeve element 268.

The outer surface 280 of the sleeve element 268 is chamfered at its second end 274 forming a reflection surface 282 as described above. Preferably the angle between the reflection surface 282 and the axis 278 of the collar 266 is between 10° and 70° and more preferably between 30° and 40°. The angle between the reflection surface 282 and the axis 278 may be more than 20° or more than 30°. The angle between the reflection surface 282 and the axis 278 may be less than 60°, less than 50° or less than 40°.

As shown most clearly in FIG. 11, in this embodiment of the sleeve element 268 a second step 307 is formed in the outer surface 280 of the first section 301 of the sleeve element 268. This second step 307 creates a further decrease in the outer diameter of the sleeve element 268 proximate the first end 272. A ledge 309 having a radially outer surface is, therefore, created extending between the first and second steps 298, 307.

The ring element 296 is tubular and has a circular cross-sectional shape. An outer surface 311 of the ring element 296 at a first end 313 is tapered. An annular rib 315 extends radially inwardly from an internal surface 317 of the ring element 296. The rib 315 is located nearer the first end 313 of the ring element 296 than a second end 319 such that a first section 325 of the ring element 296 is defined between the rib 315 and the first end 313 and a second section 327 of the ring element 296 is defined between the rib 315 and the second end 319. The rib 315 comprises a first surface 321 facing generally towards the first end 313 of the ring element 296 and an opposite second surface 323 facing generally towards the second end 319 of the ring element 296. The internal diameter of the first section 325 of the ring element 296 may be smaller than the internal diameter of the second section 327 of the ring element 296.

The attachment portion 295 of the window element 292 is received in the first end 313 of the ring element 296. As such the outer diameter of the attachment portion 295 of the window element 292 is substantially equal to the internal diameter of the first section 325 of the ring element 296. The base end face 297 of the window element 292 is in contact with the first surface 321 of the rib 315 of the ring element 296. The window element 292 is bonded to the ring element 296 by brazing, welding or fusing. Preferably the window element 292 is bonded to the ring element 296 by brazing, electron beam welding or diffusion bonding.

An end face 329 at the second end 319 of the ring element 296 seats on the abutment surface 305 of the sleeve element 268. In this embodiment a part of the internal surface of the ring element 296 at the second end 319 contacts the outer surface of the ledge 309 of the sleeve element 268. In this position, the outer surface 311 of the ring element 296 at the second end 319 is preferably continuous or contiguous with the outer surface 280 of the second section 303 of the sleeve element 268. The ring element 296 is bonded to the sleeve element 268 by brazing, welding or fusing. Preferably the ring element 296 is bonded to the sleeve element 268 by brazing, electron beam welding or diffusion bonding.

In a particularly preferred embodiment the ring element 296 and the sleeve element 268 are both made from Grade 5 titanium and the window element 292 is made from sapphire. The sapphire is bonded to the titanium ring element 296 by brazing and the ring element 296 and the sleeve element 268 are joined by electron beam welding.

Returning to FIG. 10 a screw thread 254 is provided on an external surface of the nose portion 226 of the main body 212. The optical cap 244 is secured to the main body 212 by engaging the complementary screw threads 250, 254. Once engaged, the collar 266, and in particular the sleeve element 268, of the cap 244 extends around the nose portion 226 of the main body 212. Sealing elements such as o-rings 255 may be provided to form a seal between the external surface of the nose portion 26 and the internal surface 252 of the sleeve element 268.

The optical cap 244 is screwed onto the nose portion 226 until the second end 274 of the sleeve element 268 contacts an abutment surface 275 of the nose portion 226. The length of the collar 266, between the first end 313 of the ring element 296 and the second end 274 of the sleeve element 268, is such that the first end 313 of the ring element 296 does not extend beyond the front face 243 of the lens 242. In this way the collar 266 does not block the field of view of the lens 242.

With the cap 244 secured to the main body 212 the window element 292 extends beyond the distal end face 228 of the nose portion 226. In particular the lens 242 is located in the attachment portion 295 of the window element 292 and the domed portion 293 of the window element 292 extends over the lens 242 such that there is a gap 257 between a front face 243 of the lens 242 and an internal surface 231 of the domed portion 293.

The reflection surface 282 of the collar 266 is located between the light sources 258 and the lens 242 in a longitudinal direction. The reflection surface 282 is substantially rear facing so that a fraction of the light that is emitted by the light sources 258 is incident on the reflection surface 282. The angle of the reflection surface 282 causes the light to be reflected in a direction away from the axis of the inspection assembly 210, as described above.

In other embodiments of the optical cap the collar may comprise a washer or sealing element located between the window element and the sleeve element or the ring element. The window element may be brazed or welded to one part of the sealing element and the sleeve element or the ring element may be brazed or welded to another part of the sealing element. In this way the sealing element may be chosen or designed to reduce the effects of any mismatch in coefficients of thermal expansion of the materials of the window element and the sleeve element or the ring element.

In the embodiment shown in FIGS. 10 and 11 the collar 266 includes a ring element 296 that surrounds a part of the outer surface of the window element 292 and to which the window element 292 is bonded. In other embodiments the window element may be directly bonded to the sleeve element. For example a base end face of the window element may be directly bonded to an end face at the first end of the sleeve element by diffusion bonding.

In a further embodiment the collar may comprise a metal washer element located between a base end face of the window element and an end face at the first end of the sleeve element. The window element may be diffusion bonded to the washer element, and the washer element may be electron beam welded to the sleeve element.

The present invention therefore provides an optical cap that extends over and protects a lens of an inspection assembly and is suitable for operation in downhole environments.

The invention claimed is:

1. An optical cap for a wellbore inspection assembly comprising a main body having a longitudinal axis and a forward end, a lens located at the forward end, and a light source disposed rearward of the lens and positioned to illuminate an area forward of the lens,
the optical cap comprising:
an optically clear window element comprising a domed portion and an attachment portion including an end face; and
a metal collar attached to said inspection assembly and bonded to the optically clear window element whereby, in use, light entering the lens passes through the window element of the optical cap, and at least a part of the collar surrounding the attachment portion of the window element such that, in use, a part of the collar blocks light that is emitted by the light source and that would otherwise be incident on the end face of the window element from entering the window element.

2. The optical cap as claimed in claim 1, wherein the material from which the window element is made has substantially the same coefficient of thermal expansion as the metal from which the collar is made.

3. The optical cap as claimed in claim 1, wherein the collar is bonded to the window element by means of energy beam welding, solid state welding and/or brazing.

4. The optical cap as claimed in claim 1, wherein the window element is made of sapphire, quartz or diamond.

5. The optical cap as claimed in claim 1, wherein the collar is made of titanium.

6. The optical cap as claimed in claim 1, wherein the collar is bonded to a base edge of the window element.

7. The optical cap as claimed in claim 1, wherein the collar is bonded to an external surface of the window element.

8. The optical cap as claimed in claim 1, the collar comprising a ring element and a sleeve element, wherein the ring element is bonded to the window element and the sleeve element is bonded to the ring element.

9. The optical cap as claimed in claim 8, wherein the ring element includes a radially inwardly extending rib and the window element is in contact with a first side of the rib and the sleeve element is in contact with an opposite second side of the rib.

10. The optical cap as claimed in claim 8, wherein an internal surface of a first portion of the ring element is in contact with an external surface of the window element and an internal surface of a second portion of the ring element is in contact with an external surface of the sleeve element.

11. The optical cap as claimed in claim 8, wherein an outer surface of the ring element is continuous with an outer surface of the sleeve element.

12. The optical cap as claimed in claim 8, wherein a first end of the ring element extends beyond a first end of the sleeve element, and the window element extends beyond the first end of the ring element.

13. The optical cap as claimed in claim 8, wherein the metal collar further comprises a screw thread and the screw thread is provided on an internal surface of the sleeve element.

14. The optical cap as claimed in claim 1, wherein the metal collar comprises a screw thread.

15. The optical cap as claimed in claim 1, wherein the collar comprises:
a sleeve element having first and second ends defining an axis of the collar, said window element being located proximate the first end; and
a reflection surface at the second end of the sleeve element, an angle between the reflection surface and the axis of the collar being between 10° and 70°.

16. The optical cap as claimed in claim 15, wherein the reflection surface is an unpolished surface of the collar.

17. A wellbore inspection assembly comprising:
a main body having a longitudinal axis and a forward end;
a lens located at the forward end of the main body;
a light source disposed rearward of the lens and arranged to illuminate an area forward of the lens; and
an optical cap comprising an optically clear window element and a metal collar, the window element comprising a domed portion and an attachment portion including an end face, and the collar being bonded to the window element by brazing, welding or fusing,
the optical cap being secured to the main body such that the window element extends over the lens and light entering the lens passes through the window element of the optical cap, and wherein a part of the collar blocks light that is emitted by the light source and that would otherwise be incident on the end face of the window element from entering the window element.

18. The wellbore inspection assembly as claimed in claim 17, comprising a plurality of light sources arranged around the main body and radially outward of the lens.

19. The wellbore inspection assembly as claimed in claim 18, wherein optical cap comprises a sleeve element having first and second ends, said window element being located proximate the first end and a reflection surface being provided at the second end, and wherein the reflection surface is located between the light sources and the lens.

20. A The wellbore inspection assembly as claimed in claim 17, the main body comprising a light emitting portion and a nose portion, an external diameter of the light emitting portion being greater than an external diameter of the nose portion, the light source being mounted in the light emitting portion and the lens being disposed in the nose portion, and wherein the attachment portion of the window element extends around the nose portion.

21. The wellbore inspection assembly as claimed in claim 20, comprising a plurality of light sources, each of the light sources being arranged to emit a beam of light through an aperture in the light emitting portion of the main body, and wherein centre lines of said light beams fall on a circle having a diameter greater than an external diameter of the collar of the optical cap.

22. An optical cap for a wellbore inspection assembly for use in high temperature and high pressure environments, the optical cap comprising:
- an optically clear window element comprising a domed portion and a tubular attachment portion extending from the domed portion and including an end face;
- a metal collar comprising a sleeve portion having a first, forward end and a second, rearward end an external surface of the second end of the sleeve portion being chamfered to provide a reflection surface the collar being bonded to the window element by means of brazing, welding or fusing and at least a part of the collar surrounding the attachment portion of the window element such that the second end of the sleeve portion is furthest from the domed portion of the window element, the collar further comprising a radially inwardly extending rib or flange that extends over the end face of the window element; and
- a securing portion arranged to secure the optical cap to said inspection assembly.

* * * * *